US011253372B2

(12) United States Patent (10) Patent No.: US 11,253,372 B2
Grotz (45) Date of Patent: Feb. 22, 2022

(54) UNIVERSALLY EXPANDING CAGES

(71) Applicant: iOrthopedics, Inc., Las Vegas, NV (US)

(72) Inventor: Robert Thomas Grotz, Las Vegas, NV (US)

(73) Assignee: IORTHOPEDICS, INC., Las Vegas, NV (US)

( * ) Notice: Subject to any disclaimer, the term of this patent is extended or adjusted under 35 U.S.C. 154(b) by 61 days.

(21) Appl. No.: 16/812,821

(22) Filed: Mar. 9, 2020

(65) Prior Publication Data

US 2020/0281741 A1 Sep. 10, 2020

Related U.S. Application Data

(60) Provisional application No. 62/816,075, filed on Mar. 9, 2019.

(51) Int. Cl.
*A61F 2/44* (2006.01)

(52) U.S. Cl.
CPC .... *A61F 2/4455* (2013.01); *A61F 2250/0006* (2013.01); *A61F 2250/0009* (2013.01)

(58) Field of Classification Search
CPC .......... A61F 2/44; A61F 2/4455; A61F 2/442; A61F 2/446; A61F 2/447; A61F 2/4425; A61F 2/30
See application file for complete search history.

(56) References Cited

U.S. PATENT DOCUMENTS

| 5,653,763 | A | 8/1997 | Errico et al. |
| 6,436,142 | B1 | 8/2002 | Paes et al. |
| 6,821,298 | B1 | 11/2004 | Jackson |
| 6,955,691 | B2 | 10/2005 | Chae et al. |
| 7,819,921 | B2 | 10/2010 | Grotz |
| 7,985,256 | B2 * | 7/2011 | Grotz ..................... A61F 2/4611 623/17.11 |
| 8,062,375 | B2 * | 11/2011 | Glerum ................. A61F 2/4611 623/17.16 |
| 8,663,329 | B2 * | 3/2014 | Ernst ....................... A61F 2/442 623/17.15 |
| 9,028,550 | B2 | 5/2015 | Shulock et al. |
| 9,216,095 | B2 * | 12/2015 | Glerum ................. A61F 2/4611 |
| 9,788,970 | B2 * | 10/2017 | Reimels ................ A61F 2/4465 |
| 9,937,053 | B2 * | 4/2018 | Melkent ................ A61F 2/4455 |

(Continued)

FOREIGN PATENT DOCUMENTS

| WO | 98/48739 | 11/1998 |
| WO | 2013/181024 | 12/2013 |

OTHER PUBLICATIONS

Aryan et al.; Spine surgeons share their needs and challenges; ORTHO(R)KNOW(R); pp. 1-3; Oct. 2014.

*Primary Examiner* — Christopher J Beccia
(74) *Attorney, Agent, or Firm* — Wenderoth, Lind & Ponack, L.L.P.

(57) ABSTRACT

An expandable medical implant that includes a lower lifting plate, an upper lifting plat, a distal lifting block, a proximal lifting block, a rotational block, a lifting screw, and a locking nut, and related methods of use. Also, an expandable medical implant that includes a lower lifting plate having a proximal lower angled lifting portion, an upper lifting plate having a proximal upper angled lifting portion, a center fork block, a lifting lobe, a distal screw, and a proximal nut, and related methods of use.

10 Claims, 8 Drawing Sheets

(56) References Cited

U.S. PATENT DOCUMENTS

| | | |
|---|---|---|
| 10,363,142 B2 * | 7/2019 | McClintock ............ A61F 2/447 |
| 10,575,964 B2 * | 3/2020 | Robinson .............. A61F 2/4611 |
| 10,687,963 B2 * | 6/2020 | Jimenez ................ A61F 2/447 |
| 11,051,951 B2 * | 7/2021 | Robinson ............ A61F 2/30744 |
| 11,083,595 B2 * | 8/2021 | Robinson .............. A61F 2/4425 |
| 2005/0278036 A1 | 12/2005 | Leonard et al. |
| 2010/0082109 A1 | 4/2010 | Greenhalgh et al. |
| 2013/0116791 A1 * | 5/2013 | Theofilos .............. A61F 2/4611 |
| | | 623/17.16 |
| 2014/0180419 A1 | 6/2014 | Dmuschewsky |
| 2016/0120660 A1 * | 5/2016 | Melkent ................ A61F 2/447 |
| | | 623/17.16 |
| 2016/0166396 A1 | 6/2016 | McClintock |
| 2017/0239065 A9 | 8/2017 | Reimels |

* cited by examiner

UNIVERSALLY EXPANDING CAGES

TECHNICAL FIELD

The present application generally relates to medical devices for stabilizing the vertebral motion segment or other bone segments. More particularly, the field of the disclosure relates to universally expanding cages and methods of use for providing controlled spinal correction or other bond segment spacing and/or alignment.

BACKGROUND

Spinal implants and interbody cages are conventionally used, for example, to correct deformities in the spine, stabilize the spine, fuse vertebrae, distract vertebrae, etc. Since spinal anatomy varies between patients, surgeons desire spinal implants and interbody cages that are capable of precise adjustment to accommodate such variation. However, known spinal implants and interbody cages have limited adjustments and, in particular, limit the adjustability in both the proximal and distal directions. For example, U.S. Pat. No. 10,363,142 discloses a spinal implant that has a proximal region and a distal region but has a limited range of proximal and distal expansion. Other known spinal cages, such as U.S. Pat. No. 9,028,550, offer differing ranges of adjustment, but require complicated hydraulic control systems and are limited in the adjustability in both the proximal and distal directions. Plug-style designs, such as U.S. Pat. No. 9,788,970, also lack the ability to adjust in both the proximal and distal directions. The inventors determined that there is a need for universally expanding cages that address the problems, such as those discussed above, with known spinal implants and interbody cages, such as limited adjustability.

BRIEF SUMMARY

In view of the above-mentioned exemplary problems with conventional and known cages, the present application provides universally expanding cages and methods of use.

In a first embodiment, the expandable medical implant comprises a) a lower lifting plate having an lower portion, a first lower side portion, and a second lower side portion, the first lower side portion having a first lower distal slot and a first lower proximal slot, and the second lower side portion having a second lower distal slot and a second lower proximal slot, b) an upper lifting plate having an upper portion, a first upper side portion, and a second upper side portion, the first upper side portion having a first upper distal slot and a second upper proximal slot, and the second upper side portion having a second upper distal slot and a second upper proximal slot, c) a distal lifting block having a first distal side arm and a second distal side arm, d) a proximal lifting block having a first proximal side arm and a second proximal side arm, e) a rotational block, f) a lifting screw, and g) a locking nut, wherein the lower lifting plate and the upper lifting plate slidably engage such that the first distal side arm engages with the first lower distal slot and the first upper distal slot, the second distal side arm engages with the second lower distal slot and the second upper distal slot, the first proximal side arm engages with the first lower proximal slot and the first upper proximal slot, and the second proximal side arm engages with the second lower proximal slot and the second upper proximal slot, and wherein the lifting screw engages with the distal lifting block, the rotational block, and the proximal lifting block such that the lower lifting plate and the upper lifting plate move in an upward and a downward direction by sliding the distal lifting block along the first lower distal slot, the second lower distal slot, the first upper distal slot, and the second upper distal slot and the proximal lifting block along the first lower proximal slot, the second lower proximal slot, the first upper proximal slot, and the second upper proximal slot.

In a further embodiment of the first embodiment, the lifting screw comprises external threads that engage with internal threads in each of the distal lifting block and the proximal lifting block, and wherein the lifting screw comprises an unthreaded portion that engages with the rotational block.

In a further embodiment of the first embodiment, the lifting screw comprises a stopping portion.

In a further embodiment of the first embodiment, the lifting screw has a first internal tool engagement portion.

In a further embodiment of the first embodiment, the locking nut has a second internal tool engagement portion.

In a further embodiment of the first embodiment, the first lower distal slot and the second lower distal slot are substantially parallel, the first lower proximal slot and the second lower proximal slot are substantially parallel, the first upper distal slot and the second upper distal slot are substantially parallel, and the first upper proximal slot and the second upper proximal slot are substantially parallel.

In a further embodiment of the first embodiment, the first lower distal slot is angled such that a distal end of the first lower distal slot is closer to the lower portion of the lower lifting plate than a proximal end of the first lower distal slot, the second lower distal slot is angled such that a distal end of the second lower distal slot is closer to the lower portion of the lower lifting plate than a proximal end of the second lower distal slot, the first upper distal slot is angled such that a distal end of the first upper distal slot is closer to the upper portion of the upper lifting plate than a proximal end of the first upper distal slot, the second upper distal slot is angled such that a distal end of the second upper distal slot is closer to the upper portion of the upper lifting plate than a proximal end of the second upper distal slot, the first lower proximal slot is angled such that a proximal end of the first lower proximal slot is closer to the lower portion of the lower lifting plate than a distal end of the first lower proximal slot, the second lower proximal slot is angled such that a proximal end of the second lower proximal slot is closer to the lower portion of the lower lifting plate than a distal end of the second lower proximal slot, the first upper proximal slot is angled such that a proximal end of the first upper proximal slot is closer to the upper portion of the upper lifting plate than a distal end of the first upper proximal slot, and the second upper proximal slot is angled such that a proximal end of the second upper proximal slot is closer to the upper portion of the upper lifting plate than a distal end of the second upper proximal slot.

In a further embodiment of the first embodiment, the lower portion of the lower lifting plate comprises a plurality of ridges, and wherein the upper portion of the upper lifting plate comprises a plurality of ridges.

In a further embodiment of the first embodiment, the expandable medical implant is configured such that the lower lifting plate and the upper lifting plate can be closed in both a proximal end and a distal end, opened at only the proximal end, opened at only the distal end, or opened in both the proximal end and the distal end.

In a further embodiment of the first embodiment, the lower lifting plate and the upper lifting plate each comprise a locking nut extension piece in a proximal direction.

In a second embodiment, the expandable medical implant comprises a) a lower lifting plate having a proximal lower angled lifting portion, b) an upper lifting plate having a proximal upper angled lifting portion, c) a center fork block, the center fork block engaging the lower lifting plate via a lower distal arm and at least one lower proximal trailing arm, and the center fork block engaging with the upper lifting plate via an upper distal arm and at least one upper proximal trailing arm, d) a lifting lobe, e) a distal screw, and f) a proximal nut, wherein the distal screw engages the center fork block to move a distal side of the lower lifting plate and a distal side of the upper lifting plate in an upward and a downward direction, and wherein the proximal nut engages the lifting lobe to move a proximal side of the lower lifting plate and a proximal side of the upper lifting plate in an upward and a downward direction.

In a further embodiment of the second embodiment, the center fork block has an internally threaded cavity, and the distal screw comprises external threads that engage internal threads the internally threaded cavity of the center fork block to move the center fork block in a proximal direction or a distal direction.

In a further embodiment of the second embodiment, the lifting lobe has cavity configure to allow the distal screw to pass through the lifting lobe, the proximal nut comprises internal threads that engage external threads on the distal screw to move the lifting lobe in a proximal direction and a distal direction, and the proximal nut engages the proximal lower angled lifting portion and the proximal upper angled lifting portion to move the proximal side of the lower lifting plate and the proximal side of the upper lifting plate in an upward and a downward direction.

In a further embodiment of the second embodiment, the distal screw has a first internal tool engagement portion.

In a further embodiment of the second embodiment, the proximal nut has a second internal tool engagement portion.

In a further embodiment of the second embodiment, the expandable medical implant is configured such that the lower lifting plate and the upper lifting plate can be closed in both a proximal end and a distal end, opened at only the proximal end, opened at only the distal end, or opened in both the proximal end and the distal end.

In a further embodiment of the second embodiment, the lower lifting plate comprises a plurality of ridges, and wherein the upper lifting plate comprises a plurality of ridges.

In a further embodiment of the second embodiment, the expandable medical implant is configured to allow up to 50% expansion between the lower lifting plate and the upper lifting plate.

An even further embodiment includes a method of distracting adjacent bone segments having opposing surfaces comprising inserting one or more of the expandable medical implant of the first embodiment between the opposing surfaces of the bone segments.

An even further embodiment includes a method of distracting adjacent bone segments having opposing surfaces comprising inserting one or more of the expandable medical implant of the second embodiment between the opposing surfaces of the bone segments.

BRIEF DESCRIPTION OF THE DRAWINGS

The drawings as provided for herein set forth some exemplary embodiments of the universally expanding cages and methods of the present application, the detailed description of which follows. The drawings are merely exemplary and are not intended to limit the invention.

DETAILED DESCRIPTION

First Embodiment

Figure 1:
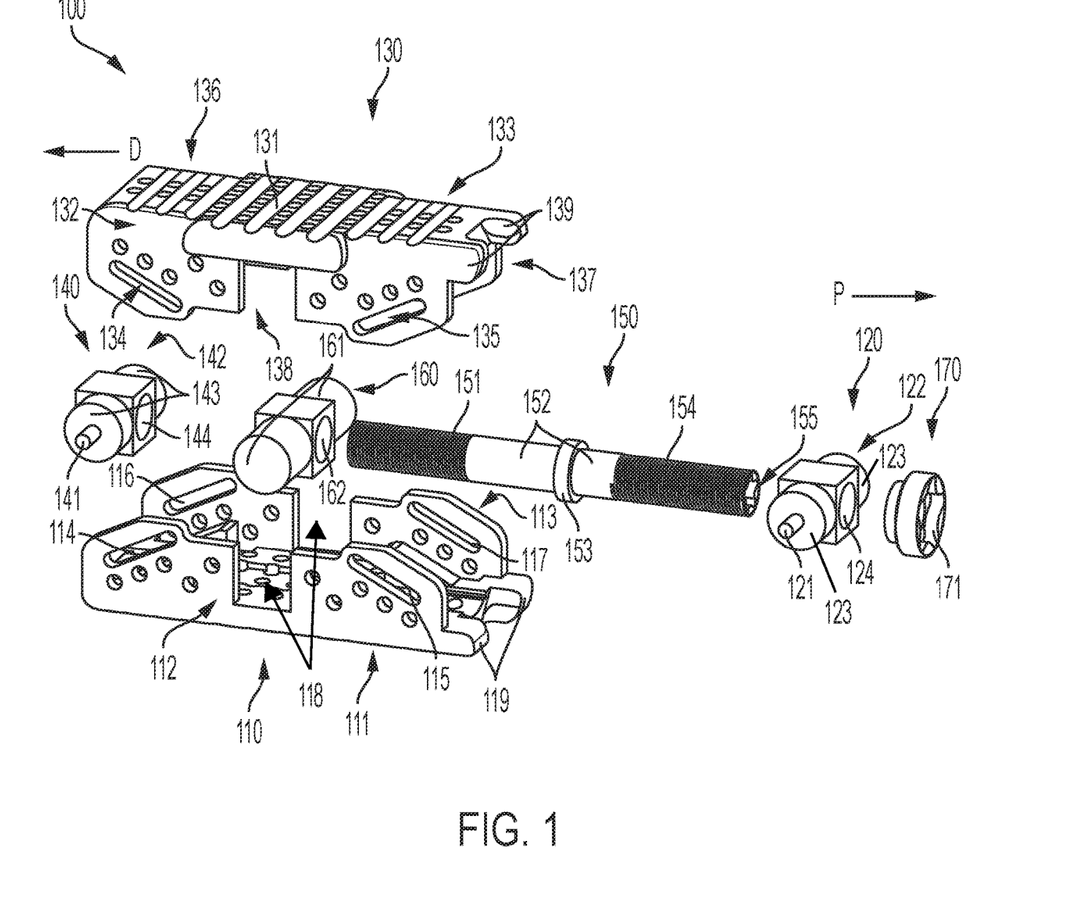
FIG. 1 is an exploded view of a first embodiment of the universally expanding cage.

FIG. 1 shows a first embodiment of the universally expanding cages. The universally expanding cages have a distal end (D) and a proximal end (P). Typically, a user, such as a surgeon, inserts the distal end (D) of the universally expanding cage into the patient, and thus the proximal end (P) is the end that is closest to the surgeon. However, such an orientation is merely exemplary. Other orientations may be adopted, despite the distal and proximal nomenclature being used herein.

In FIG. 1, an expandable medical implant (100) is shown having a lower lifting plate (110) and an upper lifting plate (130). The lower lifting plate (110) and upper lifting plate (130) each have a width such that the lower lifting plate (110) nests into the upper lifting plate (130) or, alternatively, the upper lifting plate (130) nests into the lower lifting plate (110). The lower lifting plate (110) and the upper lifting plate (130) have complementary shapes as depicted in FIG. 1.

The lower lifting plate (110) has a lower portion (111), a first lower side portion (112), and a second lower side portion (113). The lower lifting plate (110) can have a lower locking nut extension piece (119) in a proximal direction. The first lower side portion (112) has a first lower distal slot (114) and a first lower proximal slot (115), and the second lower side portion has a second lower distal slot (116) and a second lower proximal slot (117). The upper lifting plate (130) has an upper portion (131), a first upper side portion (132), and a second upper side portion (133). The upper lifting plate (110) can have an upper locking nut extension piece (139) in a proximal direction. The first upper side portion (131) has a first upper distal slot (134) and a first upper proximal slot (135), and the second upper side portion has a second upper distal slot (136) and a second upper proximal slot (137).

The expandable medical implant (100) includes a distal lifting block (140) having a first distal side arm (141) and a second distal side arm (142). The distal lifting block (140) can also include an internally threaded portion (144). The first distal side arm (141) and the second distal side arm (142) each have a length and diameter such that the first distal side arm (141) and the second distal side arm (142) sufficiently engages the first lower distal slot (114), the second lower distal slot (116), the first upper distal slot (134), and the second upper distal slot (136). Since the first distal side arm (141) and the second distal side arm (142) slidably engage with the first lower distal slot (114), the second lower distal slot (116), the first upper distal slot (134), and the second upper distal slot (136), the diameter of the first distal side arm (141) and the second distal side arm (142) should be smaller than the widths of each of the first lower distal slot (114), the second lower distal slot (116), the first upper distal slot (134), and the second upper distal slot (136) to allow for sliding movement. The distal lifting block (140) can further include one or more spacers (143). Such one or more spacers (143) can be used to reduce rotational movement of the distal lifting block (140), and center the distal lifting block (140) in between the first lower side portion (112) and the second lower side portion (113).

Further, the expandable medical implant (100) includes a proximal lifting block (120) having a first proximal side arm (121) and a second proximal side arm (122). The proximal lifting block (120) can also include an internally threaded portion (124). The first proximal side arm (121) and the second proximal side arm (122) each have a length and diameter such that the first proximal side arm (121) and the second proximal side arm (122) sufficiently engages the first lower proximal slot (115), second lower proximal slot (117), first upper proximal slot (135), and second upper proximal slot (137). Since the first proximal side arm (121) and the second proximal side arm (122) slidably engage with the first lower proximal slot (115), second lower proximal slot (117), first upper proximal slot (135), and second upper proximal slot (137), the diameter of the first proximal side arm (121) and the second proximal side arm (122) should be smaller than the widths of each of the first lower proximal slot (115), second lower proximal slot (117), first upper proximal slot (135), and second upper proximal slot (137) to allow for sliding movement. The proximal lifting block (120) can further include one or more spacers (123). Such one or more spacers (123) can be used to reduce rotational movement of the proximal lifting block (120), and center the proximal lifting block (120) in between the first lower side portion (112) and the second lower side portion (113).

The expandable medical implant (100) can include a rotational block (160). The rotational block (160) can include one or more side arms (161). The one or more side arms (161) engage with lower slots (118) in the first lower side portion (112) and a second lower side portion (113) of the lower lifting plate (110) and upper slots (138) in the first upper side portion (132) and a second upper side portion (133) of the upper lifting plate (130). Additionally, the rotational block (160) can include a cavity (162) extending from one side of the rotational block (160). The cavity (162) can be unthreaded such that the lifting screw (150), discussed below, can pass through the cavity (162).

The lifting screw (150) can include a distal threaded portion (151), an unthreaded portion (152), a stopping portion (153), and a proximal threaded portion (154). The distal threaded portion (151) can have external threads configured to engage the internally threaded portion (144) of the distal lifting block (140). The proximal threaded portion (154) can have external threads configured to engage the internally threaded portion (124) of the proximal lifting block (120). The lifting screw (150) can also include a first internal tool engagement portion (155). The first internal tool engagement portion (155) allows the surgeon to rotate the lifting screw (150) with a tool, such as a screwdriver, hex key, wrench, etc. The proximal end of the lifting screw (150) can be configured to mate with the tool. In FIG. 1, the first internal tool engagement portion (155) is depicted with a hexalobular internal profile, which is often referred to as torx or 6lobe. However, the first internal tool engagement portion (155) can utilize other internal profiles, such as slot, cross, hexagonal, square, etc. The stopping portion (153) can be affixed to lifting screw (150) such that the unthreaded portion (152) extends in a proximal and in a distal direction from the stopping portion (153). Typically, the stopping portion (153) can be located closer to the proximal end of the lifting screw (150) than the distal end of the lifting screw (150).

A locking nut (170) can be included in the expandable medical implant (100). The locking nut (170) can include internal threads that engage with the external threads of the lifting screw (150), such as the external threads of the proximal threaded portion (154). The locking nut (170) can also include a second internal tool engagement portion (171). In FIG. 1, the second internal tool engagement portion (171) is depicted with a hexalobular internal profile, which is often referred to as torx or 6lobe. However, the second internal tool engagement portion (171) can utilize other internal profiles, such as slot, cross, hexagonal, square, etc. The proximal end of the lifting screw (150) having the first internal tool engagement portion (155) can be proximally accessible through the locking nut (170) and the second internal tool engagement portion (171). Such an arrangement allows a user, such as a surgeon, to engage the lifting screw (150) when the locking nut (170) is placed onto and engaged with the lifting screw (150) thereby allowing the user to independently actuate the opening and closing of the expandable medical implant (100) at the proximal and distal ends. In an embodiment, the locking nut (170) engages the proximal threaded portion (154) to open/close the proximal end and separately the first internal tool engagement portion (155) engages the distal threaded portion (151) to open/close the distal end The lower lifting plate (110) and the upper lifting plate (130) slidably engage such that the first distal side arm (141)

engages with the first lower distal slot (114) and the first upper distal slot (134). The second distal side arm (142) engages with the second lower distal slot (116) and the second upper distal slot (136). The first proximal side arm (121) engages with the first lower proximal slot (115) and the first upper proximal slot (135). The second proximal side arm (122) engages with the second lower proximal slot (117) and the second upper proximal slot (137).

The lifting screw (150) can engage with the distal lifting block (140), the rotational block (160), and the proximal lifting block (120) such that the lower lifting plate (110) and the upper lifting plate (130) moving in an upward and downward direction by sliding the distal lifting block (140) along the first lower distal slot (114), the second lower distal slot (116), the first upper distal slot (134), and the second upper distal slot (136). Further, the proximal lifting block (120) slides along the first lower proximal slot (115), the second lower proximal slot (117), the first upper proximal slot (135), and the second upper proximal slot (137). In FIGS. 1-5, the lifting screw (150) is shown to have external threads that engage with internal threads in each of the distal lifting block (140) and the proximal lifting block (120). However, the lifting screw (150) can engage with the distal lifting block (140) and the proximal lifting block (120) using different methods, such as ridges, ratcheting, etc. The lifting screw (150) also can contain an unthread portion that engages with the rotational block (160). As noted above, the rotational block (160) can include a cavity (162) that can be unthreaded. The unthreaded portion (152) of the lifting screw (150) can pass through the cavity (162) the rotational block (160) thereby providing a pivot and support for the lifting screw (150).

Figure 2A:
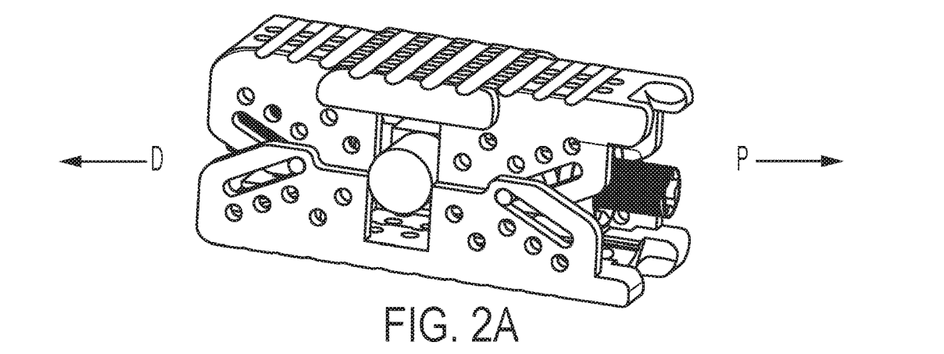
FIG. 2A is a perspective view of the first embodiment of the universally expanding cage shown in FIG. 1 showing the first embodiment of the universally expanding cage having both the proximal end and the distal end in an open position.
Figure 2B:
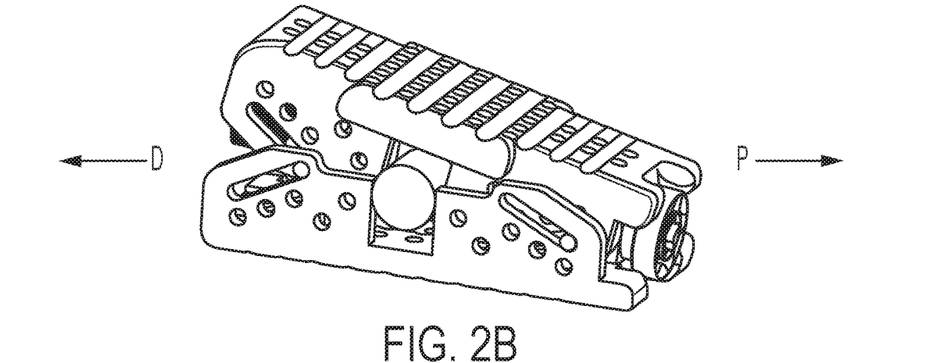
FIG. 2B is a perspective view of the first embodiment of the universally expanding cage shown in FIG. 1 showing the first embodiment of the universally expanding cage having the proximal end in a closed position and the distal end in an open position.
Figure 2C:
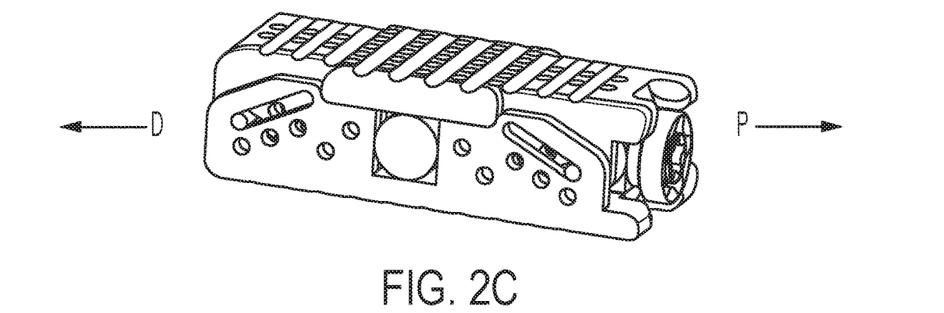
FIG. 2C is a perspective view of the first embodiment of the universally expanding cage shown in FIG. 1 showing the first embodiment of the universally expanding cage having both the proximal and the distal end in a closed position.
Figure 2D:
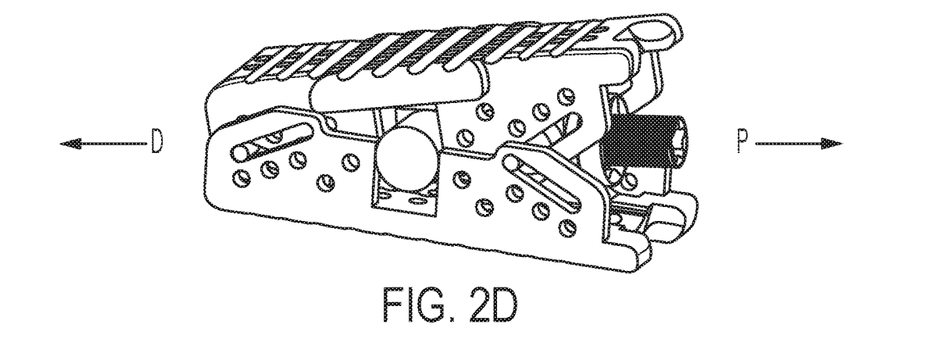
FIG. 2D is a perspective view of the first embodiment of the universally expanding cage shown in FIG. 1 showing the first embodiment of the universally expanding cage having the proximal end in an open position and the distal end in a closed position.

By adjusting the lifting screw (150) and the locking nut (170), a user, such as a surgeon, is capable of adjusting the angle between the lower lifting plate (110) and the upper lifting plate (130). FIG. 2A shows the expandable medical implant (100) having both the proximal end and the distal end in an open position. FIG. 2B shows the expandable medical implant (100) having the proximal end in a closed position and the distal end in an open position. FIG. 2C shows the expandable medical implant (100) having both the proximal and the distal end in a closed position. FIG. 2D shows the expandable medical implant (100) having the proximal end in an open position and the distal end in a closed position. FIGS. 2A-D provide examples showing the expandable medical implant (100) in completely open and closed embodiments. However, by adjusting the lifting screw (150) and the locking nut (170), the user can adjust the angle between the lower lifting plate (110) and the upper lifting plate (130) such that expandable medical implant (100) is not completely open and closed. By sliding the first distal side arm (141) and the second distal side arm (142) in their respective slots, the distance between the lower lifting plate (110) and the upper lifting plate (130) can be adjusted such that the distal end of the lower lifting plate (110) and the upper lifting plate (130) can be opened from 1% to 100% of its maximum height. Similarly, by sliding the first proximal side arm (121) and the second proximal side arm (122), the distance between the lower lifting plate (110) and the upper lifting plate (130) can be adjusted such that the proximal end of the lower lifting plate (110) and the upper lifting plate (130) can be opened from 1% to 100% of its maximum height.

Further, in FIGS. 1 and 2A-D, the first lower distal slot (114) is angled such that a distal end of the first lower distal slot (114) is closer to the lower portion (111) of the lower lifting plate (110) than a proximal end of the first lower distal slot (114). The second lower distal slot (116) is angled such that a distal end of the second lower distal slot (116) is closer to the lower portion (111) of the lower lifting plate (110) than a proximal end of the second lower distal slot. The first upper distal slot (134) is angled such that a distal end of the first upper distal slot (134) is closer to the upper portion (131) of the upper lifting plate (130) than a proximal end of the first upper distal slot (134). The second upper distal slot (136) is angled such that a distal end of the second upper distal slot (136) is closer to the upper portion (131) of the upper lifting plate (130) than a proximal end of the second upper distal slot (136).

The first lower proximal slot (115) is angled such that a proximal end of the first lower proximal slot (115) is closer to the lower portion (111) of the lower lifting plate (110) than a distal end of the first lower proximal slot (115). The second lower proximal slot (117) is angled such that a proximal end of the second lower proximal slot (117) is closer to the lower portion (111) of the lower lifting plate (110) than a distal end of the second lower proximal slot (117). The first upper proximal slot (135) is angled such that a proximal end of the first upper proximal slot (135) is closer to the upper portion (131) of the upper lifting plate (130) than a distal end of the first upper proximal slot (135). The second upper proximal slot (137) is angled such that a proximal end of the second upper proximal slot (137) is closer to the upper portion (131) of the upper lifting plate (130) than a distal end of the second upper proximal slot (137).

As seen in FIGS. 1 and 2A-D, each of the angles of the first lower distal slot (114), the second lower distal slot (116), the first lower proximal slot (115), the second lower proximal slot (117), the first upper distal slot (134), the second upper distal slot (136), first upper proximal slot (135), and the second upper proximal slot (137) are approximately the same. However, such angles can be adjusted during manufacturing to increase or decrease the maximum and minimum angles between the lower lifting plate (110) and the upper lifting plate (130) in addition to the distance between the lower lifting plate (110) and the upper lifting plate (130). In FIGS. 1 and 2A-D, the angle shown is approximately 30°, but other acceptable angles include, for example, 10°, 20°, 40°, 50°, 60°, 70°, and 80°. In addition, each of the slots on the distal side and the slots on the proximal side can differ or be the same. Typically, corresponding slots on the lower lifting plate (110) and the upper lifting plate (130), such as the first lower distal slot (114) and the first upper distal slot (134), have approximately the same angles, but, in certain embodiments, such corresponding angles can differ to achieve particular maximum and minimum angles between the lower lifting plate (110) and the upper lifting plate (130) in addition to achieving particular distances between the lower lifting plate (110) and the upper lifting plate (130). The expandable medical implant (100) can have a length, width, and height appropriately selected for use in a spinal column. For example, the length can be in the range of 20 mm to 35 mm, including, for example, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, and 35 mm. For example, the width can be 7 mm to 13 mm, including, for example, 7 mm, 8 mm, 9 mm, 10 mm, 11 mm, 12 mm, and 13 mm. For example, the height can be in the range of 7 mm to 17 mm, including, for example, 7 mm, 8 mm, 9 mm, 10 mm, 11 mm, 12 mm, 13 mm, 14 mm, 15 mm, 16 mm, and 17 mm. Also, the height difference between the open state (i.e., FIG. 2A) and the closed state (i.e., FIG. 2C) can be up to 50%, but can also be up to 10%, 20%, 30%, and 40%.

Further, corresponding slots, such as the first lower distal slot (114) and the second lower distal slot (116), the first lower proximal slot (115) and the second lower proximal slot (117), the first upper distal slot (134) and the second upper distal slot (136), and the first upper proximal slot (135) and the second upper proximal slot (137), are substantially parallel. These corresponding slots also typically have substantially the same length and the same width. However, in certain embodiments, the aforementioned corresponding slots can be adjusted such that the corresponding slots are not substantially parallel, thereby resulting in the lower lifting plate (110) and the upper lifting plate (130) having a side tilt.

The lower portion (111) of the lower lifting plate (110) can contain a plurality of ridges. Similarly, the upper portion (131) of the upper lifting plate (130) can also contain a plurality of ridges. Such ridges on the lower lifting plate (110) and/or the upper lifting plate (130) assisting in securing the lower lifting plate (110) and/or the upper lifting plate (130) to bone surfaces. Even though ridges are shown in FIGS. 1 and 2A-D, ridges are not required, but rather other surfaces can be utilized to similarly assist in securing the lower lifting plate (110) and/or the upper lifting plate (130) to bone surfaces, such as surface roughening, bumps, etc.

The expandable medical implant (100) can be made from materials that are appropriate for medical implants, such as, for example, titanium, alloys, 3D manufactured materials, polyetheretherketone (PEEK), composites with PEEK include calcium silicate, bioglass, and β-tricalcium phosphate (β-TCP), osteoconductive materials, such as bioceramics, and combinations thereof. For instance, the lower lifting plate (110) and the upper lifting plate (130) could be made from polyetheretherketone, but the lifting screw (150) and the locking nut (170) could be made from titanium alloys. Additionally, the expandable medical implant (100) can be filled with a bone-growth promoting material, such as beta-tricalcium phosphate or a bone autograft or allograft. Other compositions that could be included with the implant including, for example, bone graft substitutes, such as Interpore (sea) coral that has a trabecular spacial design amenable to osteophyte ingress, and bio-absorbables, such as α-polyesters and isomers thereof, in particular polylactide acids (PLAs). The expandable medical implant (100) can also be coated with, for example, hydroxyapatite.

The expandable medical implant (100) can be used in a variety of circumstances. For instance, the expandable medical implant (100) can be used to separate adjacent vertebral bodies when, for example, the intervertebral disc between the adjacent vertebral bodies deteriorates, herniates, or is otherwise damaged. Such a method involves distracting adjacent bone segments having opposing surfaces involves inserting one or more of the expandable medical implant discussed above between the opposing surfaces of the bone segments. Typically, the surgeon will adjust the expandable medical implant (100) to the appropriate angle between the lower lifting plate (110) and the upper lifting plate (130) before insertion. However, in some circumstances, the surgeon can insert the expandable medical implant (100) and then adjust the angle between the lower lifting plate (110) and the upper lifting plate (130) after insertion. Adjusting the angle after insertion can reduce the impact to the body since the expandable medical implant (100) can be inserted in its smallest, collapsed form via a small incision, and can also avoid impacting surrounding tissue and nerves.

The method can involve the insertion of a single expandable medical implant (100) or a plurality thereof. Even though the expandable medical implant (100) can be typically inserted posteriorly, the expandable medical implant (100) can be inserted from any direction permitted by the surrounding anatomy. To prevent movement after implantation, in some implementations a biocompatible adhesive or thread locking compound may be applied to the expandable medical implant (100).

Second Embodiment

Figure 3:
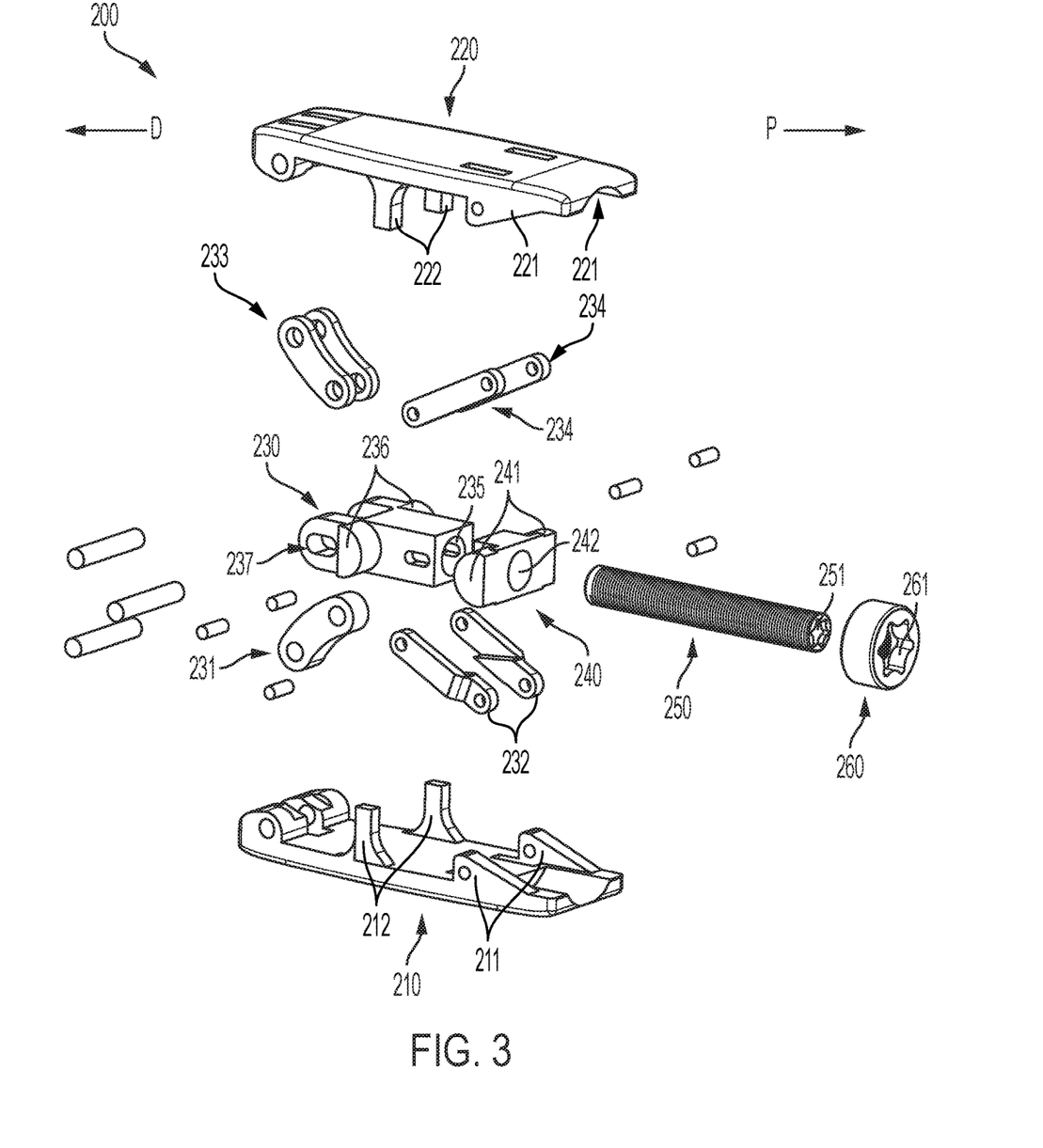
FIG. 3 is an exploded view of a second embodiment of the universally expanding cage.

FIG. 3 shows a second embodiment of the universally expanding cages. The universally expanding cages have a distal end (D) and a proximal end (P). Typically, a user, such as a surgeon, inserts the distal end (D) of the universally expanding cage into the patient, and thus the proximal end (P) is the end that is closest to the surgeon. However, such an orientation is merely exemplary. Other orientations may be adopted, despite the distal and proximal nomenclature being used herein.

In FIG. 3, an expandable medical implant (200) is shown having a lower lifting plate (210) and an upper lifting plate (220). The lower lifting plate (210) can have a proximal lower angled lifting portion (211). The upper lifting plate can have a proximal upper angled lifting portion (221). FIG. 3 shows an exemplary embodiment of the expandable medical implant (200) where each of proximal lower angled lifting portion (211) and the proximal upper angled lifting portion (221) has an angle of approximately 30°, but other acceptable angles include, for example, 10°, 20°, 40°, 50°, 60°, 70°, and 80°.

The expandable medical implant (200) can include a center fork block (230). The center fork block (230) can engage the lower lifting plate (210) via a lower distal arm (231) and at least one lower proximal trailing arm (232), but as depicted in FIG. 3, a plurality of lower proximal trailing arms (232) is also acceptable. The center fork block (230) can engage the upper lifting plate (220) via an upper distal arm (233) and at least one upper proximal trailing arm (234), but as depicted in FIG. 3, a plurality of upper proximal trailing arms (234) is also acceptable. The center fork block (230) can include a cavity (235), which can be internally threaded, extending through the body of the center fork block (230). Also, the center fork block (230) can have one or more side arms (236). As seen in FIG. 3, the one or more side arms (236) can have a semicylindrical shape. The shape of the one or more side support arms (236) can correspond to the shape of the base of the side posts (212, 222) on the lower lifting plate (210) and the upper lifting plate (220).

The center fork block (230) can include one or more knuckles (237) on the distal side of the center fork block (230). The one or more knuckles (237) can include a hole configured to accept a pin. The upper distal arm (233) can engage the center fork block (230) via the one or more knuckles (237) and be secured with, for example, a pin. The upper distal arm (233) can engage with the upper lifting plate (220) on the side opposite to the side that engages the center fork block (230) and also be secured to the upper lifting plate (220) with, for example, a pin. The lower distal arm (231) can also engage the center fork block (230) via the one or more knuckles (237) and be secured with, for example, a pin. The lower distal arm (231) can engage with the lower lifting plate (210) on the side opposite to the side that engages the center fork block (230) and also be secured to the lower lifting plate (210) with, for example, a pin. As depicted in FIG. 3, the lower distal arm (231) can nest inside of the upper distal arm (233) at the one or more knuckles (237) on the distal side of the center fork block (230). By doing so, both the lower distal arm (231) and the upper distal arm (233) can engage the center fork block (230) via one or more knuckles (237). When the center fork block (230) is moved in a distal direction, the distal end of the lower lifting plate (210) and the distal end of the upper lifting plate (220) move apart. When the center fork block (230) is moved in a proximal direction, the distal end of the lower lifting plate (210) and the distal end of the upper lifting plate (220) move closer to each other.

The center fork block (230) can engage the upper lifting plate (220) at the proximal end of the upper lifting plate (220) via a plurality of upper proximal trailing arms (234). The center fork block (230) can engage also the lower lifting plate (210) at the proximal end of the lower lifting plate (210) via a plurality of lower proximal trailing arms (232). The plurality of upper proximal trailing arms (234) and the plurality of lower proximal trailing arms (232) can be secured to the center fork block (230) via, for example, pins that engage pin accepter holes in the sides of the center fork block (230). Similarly, the plurality of upper proximal trailing arms (234) and plurality of lower proximal trailing arms (232) can be secured to the upper lifting plate (220) and the lower lifting plate (210), respectively, via, for example, pins that engage pin accepter holes in the upper lifting plate (220) and the lower lifting plate (210). When the center fork block (230) is moved in a distal direction, the proximal end of the lower lifting plate (210) and the proximal end of the upper lifting plate (220) move closer to each other. When the center fork block (230) is moved in a proximal direction, the proximal end of the lower lifting plate (210) and the proximal end of the upper lifting plate (220) move apart.

The expandable medical implant (200) can include a lifting lobe (240). The lifting lobe (240) can have a plurality of side arms (241). As depicted in FIG. 3, the plurality of side arms (241) can be in a semicylindrical shape, but can also have different profiles as desired, such as an oblong profile. The lifting lobe (240) can have a cavity (242) that can be threaded to engage threads on the distal screw (250), but also can be unthreaded such that the distal screw (250) can pass through the lifting lobe (240). When moved in a distal and proximal direction, the lifting lobe (240) can engage with the proximal lower angled lifting portion (211) and the proximal upper angled lifting portion (221) to exert force the upper lifting plate (220) and the lower lifting plate (210). When the lifting lobe (240) is moved in a distal direction, the lifting lobe (240) engages with the proximal lower angled lifting portion (211) and the proximal upper angled lifting portion (221) to force the upper lifting plate (220) and the lower lifting plate (210) apart. When the lifting lobe (240) is moved in a proximal direction, the lifting lobe (240) engages with the proximal lower angled lifting portion (211) and the proximal upper angled lifting portion (221) to allow the upper lifting plate (220) and the lower lifting plate (210) to come closer to each other.

The expandable medical implant (200) can include a distal screw (250). The distal screw can have external threads that can engage with the internal threads of the center fork block (230) and the proximal nut (260), discussed below. The distal screw (250) can also include a first internal tool engagement portion (251). The first internal tool engagement portion (251) allows the surgeon to rotate the distal screw (250) with a tool, such as a screw driver, hex key, wrench, etc. By rotating the distal screw (250), the surgeon can adjust the distance between the upper lifting plate (220) and the lower lifting plate (210). In FIG. 3, the first internal tool engagement portion (251) is depicted with a hexalobular internal profile, which is often referred to as torx or 6lobe. However, the first internal tool engagement portion (251) can utilize other internal profiles, such as slot, cross, hexagonal, square, etc.

The expandable medical implant (200) can include a proximal nut (260). The proximal nut (260) can include internal threads that engage with the external threads of the distal screw (250). The proximal nut (260) can also include a second internal tool engagement portion (261). In FIG. 3, the second internal tool engagement portion (261) is depicted with a hexalobular internal profile, which is often referred to as torx or 6lobe. However, the second internal tool engagement portion (261) can utilize other internal profiles, such as slot, cross, hexagonal, square, etc. The proximal nut (260) can engage the lifting lobe (240) to move a proximal side of the lower lifting plate (210) and a proximal side of the upper lifting plate (220) in an upward and a downward direction.

Figure 5A:
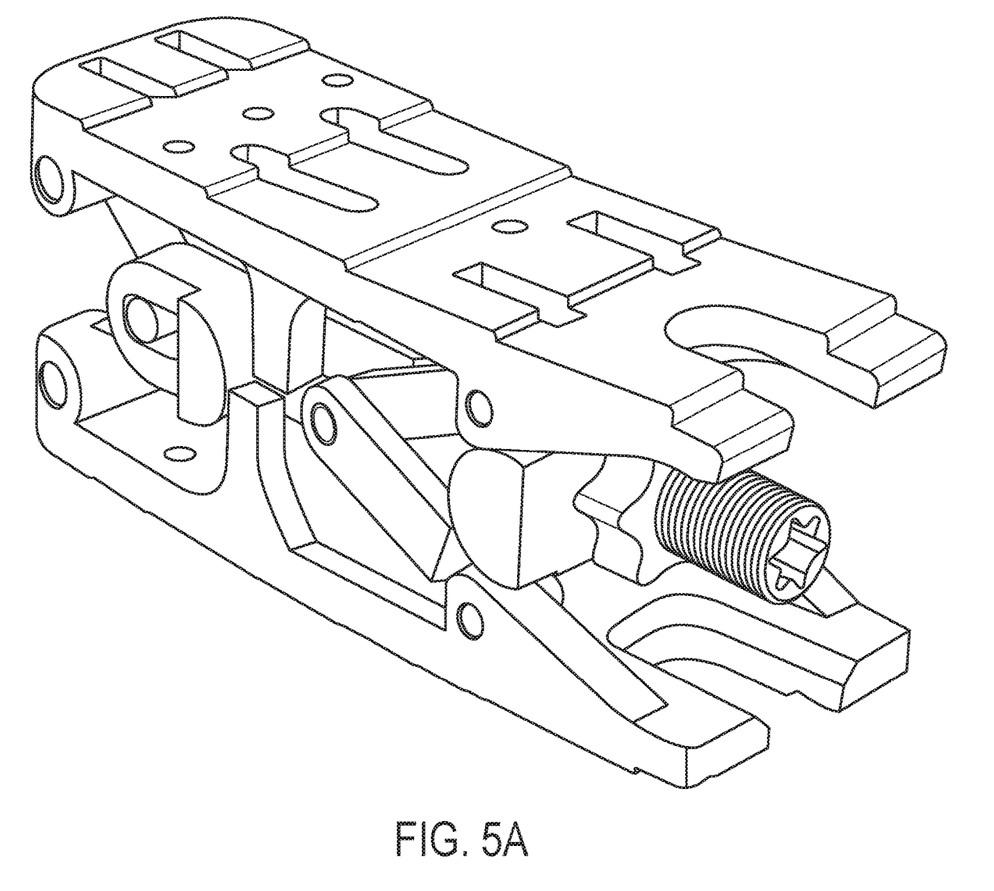
FIG. 5A is a perspective view of the second embodiment of the universally expanding cage shown in FIG. 3 showing the second embodiment of the universally expanding cage having both the proximal end and the distal end in an open position.
Figure 5B:
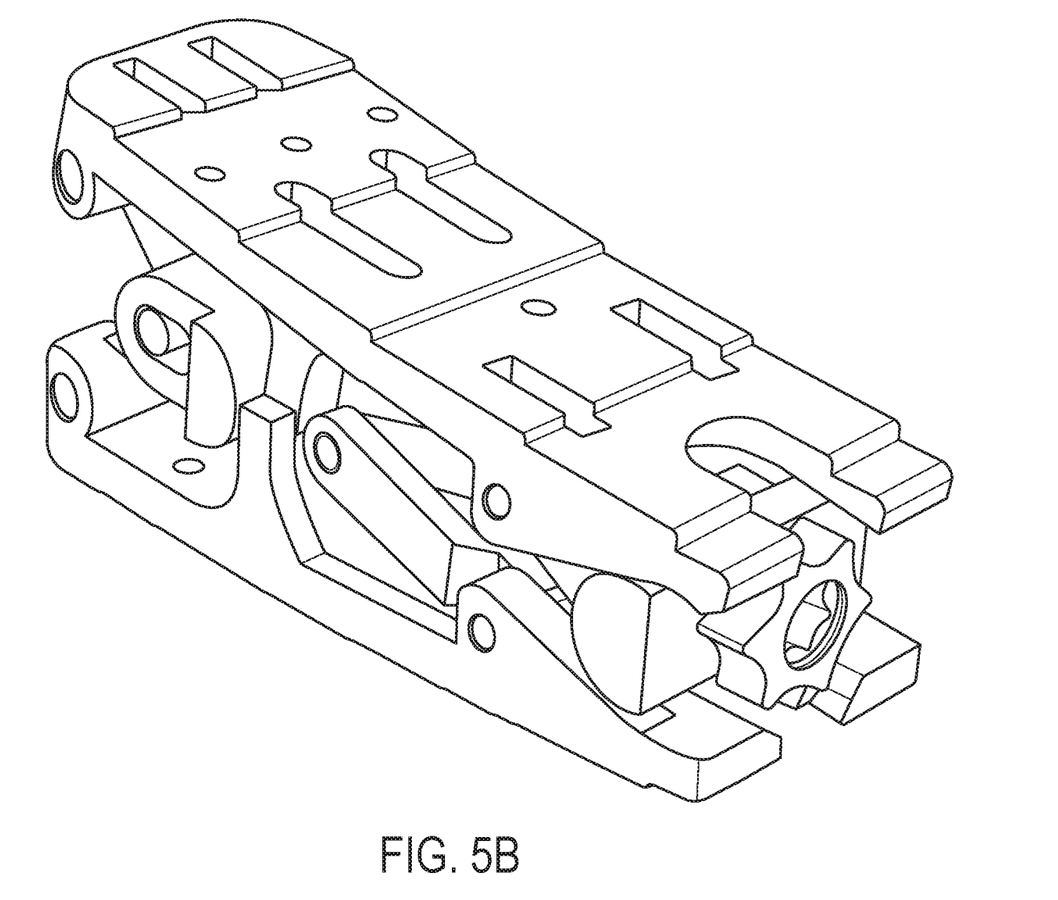
FIG. 5B is a perspective view of the second embodiment of the universally expanding cage shown in FIG. 3 showing the second embodiment of the universally expanding cage having the proximal end in a closed position and the distal end in an open position.
Figure 5C:
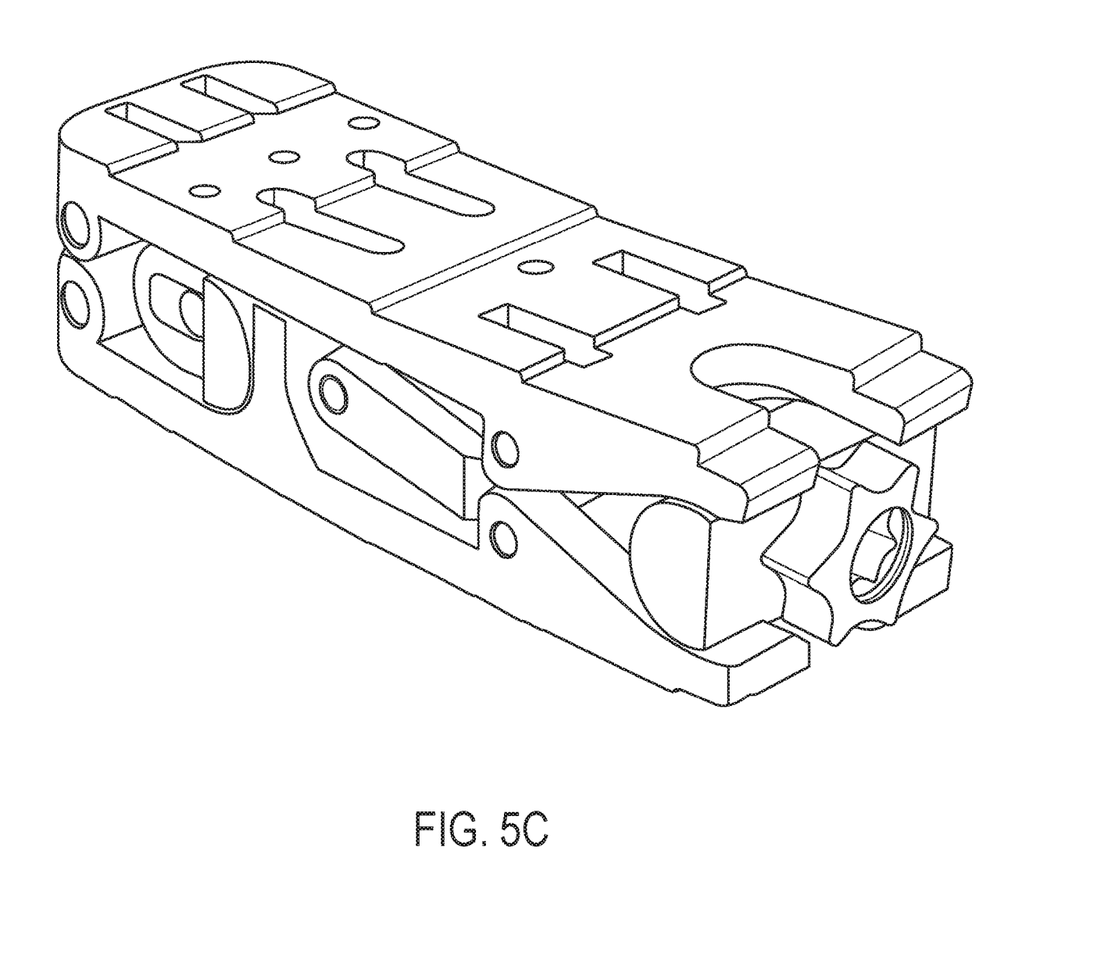
FIG. 5C is a perspective view of the second embodiment of the universally expanding cage shown in FIG. 3 showing the second embodiment of the universally expanding cage having both the proximal and the distal end in a closed position.
Figure 5D:
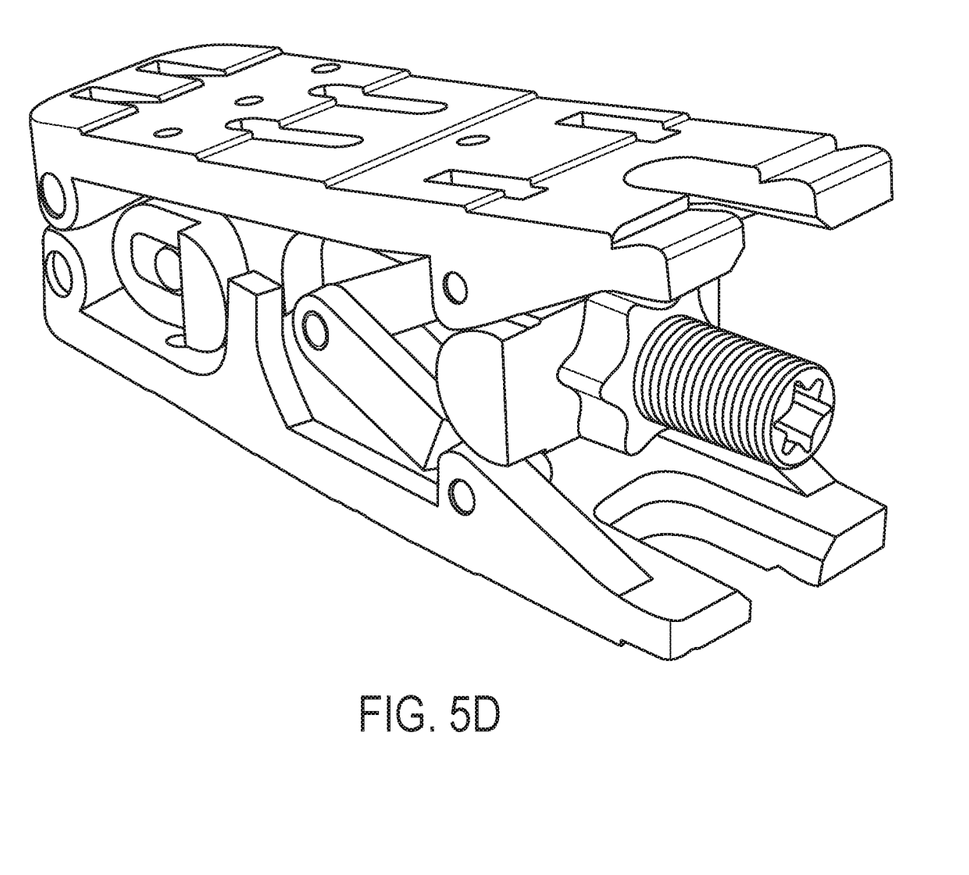
FIG. 5D is a perspective view of the second embodiment of the universally expanding cage shown in FIG. 3 showing the second embodiment of the universally expanding cage having the proximal end in an open position and the distal end in a closed position.

By adjusting the distal screw (250) and the proximal nut (260), a user, such as a surgeon, is capable of adjusting the angle between the lower lifting plate (210) and the upper lifting plate (220). FIG. 5A shows the expandable medical implant (200) having both the proximal end and the distal end in an open position. FIG. 5B shows the expandable medical implant (200) having the proximal end in a closed position and the distal end in an open position. FIG. 5C shows the expandable medical implant (200) having both the proximal and the distal end in a closed position. FIG. 5D shows the expandable medical implant (200) having the proximal end in an open position and the distal end in a closed position. FIGS. 5A-D provide examples showing the expandable medical implant (100) in completely open and closed embodiments. However, by adjusting the distal screw (250) and the proximal nut (260), the user can adjust the angle between the lower lifting plate (210) and the upper lifting plate (220) such that expandable medical implant (200) is not completely open and closed. Also, the height difference between the open state (i.e., FIG. 5A) and the closed state (i.e., FIG. 5C) can be up to 50%, but can also be up to 10%, 20%, 30%, and 40%.

Figure 4A:
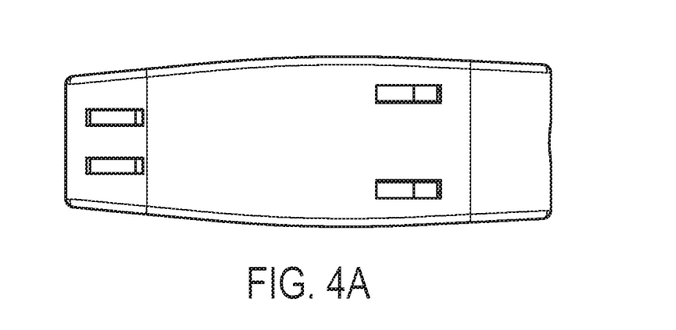
FIG. 4A is a top view of the second embodiment of the universally expanding cage shown in FIG. 3.
Figure 4B:
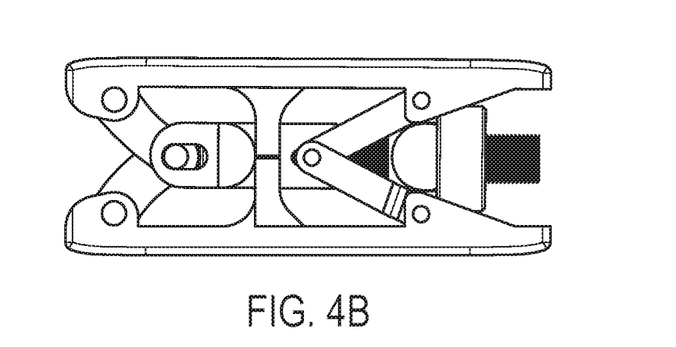
FIG. 4B is a side view of the second embodiment of the universally expanding cage shown in FIG. 3.
Figure 4C:
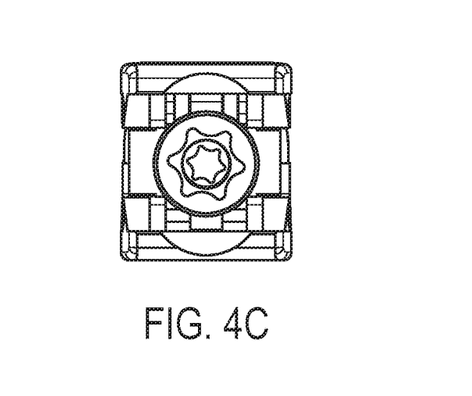
FIG. 4C is an end view of the second embodiment of the universally expanding cage shown in FIG. 3.

The lower lifting plate (210) can contain a plurality of ridges, even though the top view shown in FIG. 4A does not contain such ridges. Similarly, the upper lifting plate (220) can also contain a plurality of ridges, but also does not require such ridges. Such ridges on the lower lifting plate (210) and/or the upper lifting plate (220) assisting in securing the lower lifting plate (210) and/or the upper lifting plate (220) to bone surfaces. Even though ridges are mentioned above, ridges are not required, but rather other surfaces can be utilized to similarly assist in securing the lower lifting plate (210) and/or the upper lifting plate (220) to bone surfaces, such as surface roughening, bumps, etc.

The expandable medical implant (200) can be made from materials that are appropriate for medical implants, such as, for example, titanium, alloys, 3D manufactured materials, polyetheretherketone (PEEK), composites with PEEK include calcium silicate, bioglass, and β-tricalcium phosphate (β-TCP), osteoconductive materials, such as bioceramics, and combinations thereof. For instance, the lower lifting plate (210) and the upper lifting plate (220) could be made from polyetheretherketone, but the distal screw (250) and the proximal nut (260) could be made from titanium alloys. Additionally, the expandable medical implant (200) can be filled with a bone-growth promoting material, such as beta-tricalcium phosphate or a bone autograft or allograft. Other compositions that could be included with the implant including, for example, bone graft substitutes, such as Interpore (sea) coral that has a trabecular spacial design amenable to osteophyte ingress, and bio-absorbables, such as α-polyesters and isomers thereof, in particular polylactide acids (PLAs). The expandable medical implant (200) can also be coated with, for example, hydroxyapatite.

The expandable medical implant (200) can be used in a variety of circumstances. For instance, the expandable medical implant (200) can be used to separate adjacent vertebral bodies when, for example, the intervertebral disc between the adjacent vertebral bodies deteriorates, herniates, or is otherwise damaged. Such a method involves distracting adjacent bone segments having opposing surfaces involves inserting one or more of the expandable medical implant discussed above between the opposing surfaces of the bone segments. Typically, the surgeon will adjust the expandable medical implant (200) to the appropriate angle between the lower lifting plate (210) and the upper lifting plate (220) before insertion. However, in some circumstances, the surgeon can insert the expandable medical implant (200) and then adjust the angle between the lower lifting plate (210) and the upper lifting plate (220) after insertion. Adjusting the angle after insertion can reduce the impact to the body since the expandable medical implant (200) can be inserted in its smallest, collapsed form via a small incision, and can also avoid impacting surrounding tissue and nerves.

The method can involve the insertion of a single expandable medical implant (200) or a plurality thereof. Even though the expandable medical implant (200) can be typically inserted posteriorly, the expandable medical implant (200) can be inserted from any direction permitted by the surrounding anatomy. To prevent movement after implantation, in some implementations a biocompatible adhesive or thread locking compound may be applied to the expandable medical implant (200).

In the foregoing description, the expandable medical implants and methods of the present application have been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification, unless the context requires otherwise, the word "comprise" and its variations, such as "comprises" and "comprising," will be understood to imply the inclusion of a stated item, element or step or group of items, elements or steps, but not the exclusion of any other item, element or step or group of items, elements or steps. Furthermore, the indefinite article "a" or "an" is meant to indicate one or more of the item, element or step modified by the article.

The invention claimed is:

1. An expandable medical implant comprising
  a) a lower lifting plate having a lower portion, a first lower side portion, and a second lower side portion, the first lower side portion having a first lower distal slot and a first lower proximal slot, and the second lower side portion having a second lower distal slot and a second lower proximal slot,
  b) an upper lifting plate having an upper portion, a first upper side portion, and a second upper side portion, the first upper side portion having a first upper distal slot and a second upper proximal slot, and the second upper side portion having a second upper distal slot and a second upper proximal slot,
  c) a distal lifting block having a first distal side arm and a second distal side arm,
  d) a proximal lifting block having a first proximal side arm and a second proximal side arm,
  e) a rotational block,
  f) a lifting screw, and
  g) a locking nut,
  wherein the lower lifting plate and the upper lifting plate slidably engage such that the first distal side arm engages with the first lower distal slot and the first upper distal slot, the second distal side arm engages with the second lower distal slot and the second upper distal slot, the first proximal side arm engages with the first lower proximal slot and the first upper proximal slot, and the second proximal side arm engages with the second lower proximal slot and the second upper proximal slot, and
  wherein the lifting screw engages with the distal lifting block, the rotational block, and the proximal lifting block such that the lower lifting plate moves in an upward direction relative to the lifting screw and the lower lifting plate moves in a downward direction relative to the lifting screw by sliding the distal lifting block along the first lower distal slot, the second lower distal slot, the first upper distal slot, and the second upper distal slot and the proximal lifting block along the first lower proximal slot, the second lower proximal slot, the first upper proximal slot, and the second upper proximal slot.

2. The expandable medical implant of claim 1, wherein the lifting screw comprises external threads that engage with internal threads in each of the distal lifting block and the proximal lifting block, and wherein the lifting screw comprises an unthreaded portion that engages with the rotational block.

3. The expandable medical implant of claim 1, wherein the lifting screw comprises a stopping portion.

4. The expandable medical implant of claim 1, wherein the lifting screw has a first internal tool engagement portion.

5. The expandable medical implant of claim 1, wherein the locking nut has a second internal tool engagement portion.

6. The expandable medical implant of claim 1, wherein
  the first lower distal slot and the second lower distal slot are substantially parallel,
  the first lower proximal slot and the second lower proximal slot are substantially parallel,
  the first upper distal slot and the second upper distal slot are substantially parallel, and
  the first upper proximal slot and the second upper proximal slot are substantially parallel.

7. The expandable medical implant of claim 1, wherein
  the first lower distal slot is angled such that a distal end of the first lower distal slot is closer to the lower portion of the lower lifting plate than a proximal end of the first lower distal slot,
  the second lower distal slot is angled such that a distal end of the second lower distal slot is closer to the lower portion of the lower lifting plate than a proximal end of the second lower distal slot,
  the first upper distal slot is angled such that a distal end of the first upper distal slot is closer to the upper portion of the upper lifting plate than a proximal end of the first upper distal slot,
  the second upper distal slot is angled such that a distal end of the second upper distal slot is closer to the upper portion of the upper lifting plate than a proximal end of the second upper distal slot, the first lower proximal slot is angled such that a proximal end of the first lower proximal slot is closer to the lower portion of the lower lifting plate than a distal end of the first lower proximal slot, the second lower proximal slot is angled such that a proximal end of the second lower proximal slot is closer to the lower portion of the lower lifting plate than a distal end of the second lower proximal slot, the first upper proximal slot is angled such that a proximal end of the first upper proximal slot is closer to the upper portion of the upper lifting plate than a distal end of the first upper proximal slot, and the second upper proximal slot is angled such that a proximal end of the second upper proximal slot is closer to the upper portion of the upper lifting plate than a distal end of the second upper proximal slot.

8. The expandable medical implant of claim 1, wherein the lower portion of the lower lifting plate comprises a plurality of ridges, and wherein the upper portion of the upper lifting plate comprises a plurality of ridges.

9. The expandable medical implant of claim 1, wherein the expandable medical implant is configured such that the lower lifting plate and the upper lifting plate can be closed in both a proximal end and a distal end, opened at only the proximal end, opened at only the distal end, or opened in both the proximal end and the distal end.

10. The expandable medical implant of claim 1, wherein the lower lifting plate and the upper lifting plate each comprise a locking nut extension piece in a proximal direction.

* * * * *